United States Patent [19]
Fults

[11] Patent Number: 6,017,308
[45] Date of Patent: Jan. 25, 2000

[54] BLOOD ALCOHOL CONTENT MONITORING DEVICE

[76] Inventor: Steven P. Fults, 190 N. Griffith St., Manchester, Pa. 17345

[21] Appl. No.: 09/081,042

[22] Filed: May 19, 1998

[51] Int. Cl.[7] .................................................... A61F 15/42
[52] U.S. Cl. ............................................................ 600/300
[58] Field of Search ..................................... 600/300, 301

[56] References Cited

U.S. PATENT DOCUMENTS

| | | | |
|---|---|---|---|
| 3,668,866 | 6/1972 | Lund | 58/152 |
| 4,775,780 | 10/1988 | Ross, Jr. | 235/89 A |
| 4,797,539 | 1/1989 | Forest | 235/85 R |
| 5,157,601 | 10/1992 | Jones et al. | 364/413.11 |
| 5,274,550 | 12/1993 | Greenlee | 364/413.09 |

*Primary Examiner*—Robert L. Nasser
*Attorney, Agent, or Firm*—Aquilino, Welsh & Flaxman

[57] ABSTRACT

A blood alcohol content monitoring device is disclosed. The device includes a microcontroller storing body characteristic information of an individual and alcoholic beverage information, a clock for measuring the passage of time and a user interface coupled to the microcontroller such that a user may input body characteristic information and alcoholic beverage information for use by the microcontroller. The microcontroller further includes calculation means for calculating the blood alcohol content of the individual based upon body characteristic information, alcoholic beverage information and the passage of time. The calculation means also estimates the blood alcohol content of an individual if the individual were to have an additional drink. The user interface includes a display coupled to the microcontroller for providing the individual with information regarding blood alcohol content based upon the body characteristic information, alcoholic beverage information and the passage of time. The display also provides the individual with a message regarding the estimated blood alcohol content if the individual were to have an additional drink and provides an indication of the time required to elapse before the individual can consume their next drink without exceeding the preset target blood alcohol content.

20 Claims, 5 Drawing Sheets

BLOOD ALCOHOL CONTENT MONITORING DEVICE

BACKGROUND OF THE INVENTION

1. Field of the Invention

The invention relates to a blood alcohol content monitoring device. More particularly, the invention relates to a blood alcohol content monitoring device which provides warnings as an individual is prepared to take a drink that would place him or her beyond a preselected blood alcohol content.

2. Description of the Prior Art

Alcohol is a contributing factor to many accidents. As individuals drink, their blood alcohol content rises. The increase in their blood alcohol content impairs their ability to control themselves and their surroundings. Unfortunately, as individuals drink more and more, their ability to appreciate the risks they encounter decreases. The failure to appreciate the risks associated with their drinking often leads individuals to drink more and more without understanding the intoxication level they are reaching. As such, these individuals fail to fully appreciate the dangerous environment which they are creating with their continued drinking.

This problem is especially pronounced when people drink and drive. As individuals drink a small amount, they often do not appreciate their impaired coordination. They also do not appreciate the gradual decrease in coordination when they simply have an additional drink.

It is, therefore, desirable for individuals to monitor their blood alcohol content while they drink alcohol so they are warned when they reach an unsafe blood alcohol content level. Prior devices have attempted to address the issue of monitoring blood alcohol content. However, these devices are generally difficult to operate, do not provide individuals with all the information they require and are quite cumbersome in size.

A need, therefore, exists for a blood alcohol content monitoring device which is convenient to use and provides users with relevant information they require. The present invention provides such a blood alcohol content monitoring device.

SUMMARY OF THE INVENTION

It is, therefore, an object of the present invention to provide a blood alcohol content monitoring device. The device includes a microcontroller storing body characteristic information of an individual and alcoholic beverage information, a clock for measuring the passage of time and a user interface coupled to the microcontroller such that a user may input body characteristic information and alcoholic beverage information for use by the microcontroller. The microcontroller further includes calculation means for calculating the blood alcohol content of the individual based upon body characteristic information, alcoholic beverage information and the passage of time. The calculation means also estimates the blood alcohol content of an individual if the individual were to have an additional drink. The user interface includes a display coupled to the microcontroller for providing the individual with information regarding blood alcohol content based upon the body characteristic information, alcoholic beverage information and the passage of time. The display also provides the individual with a message regarding the estimated blood alcohol content if the individual were to have an additional drink.

It is a further object of the present invention to provide a blood alcohol content monitoring device wherein the display provides the blood alcohol content of the individual if the individual were to have an additional drink.

It is also an object of the present invention to provide a blood alcohol content monitoring device wherein the calculation means also determines when an individual will exceed an established blood alcohol content by having an additional drink and the display provides the individual with a warning when the individual will exceed an established blood alcohol content by having an additional drink.

It is another object of the present invention to provide a blood alcohol content monitoring device wherein the microcontroller stores an established blood alcohol content and the user interface includes means for inputting a target blood alcohol content. In addition, the display provides the individual with a warning when the individual will exceed the target blood alcohol content by having an additional drink.

It is also an object of the present invention to provide a blood alcohol content monitoring device wherein the warning includes a report as to how long the individual must wait before having an additional drink without exceeding the target blood alcohol content.

It is another object of the present invention to provide a blood alcohol content monitoring device wherein the user interface includes at most three keys for inputting body characteristic information and alcoholic beverage information.

It is a further object of the present invention to provide a blood alcohol content monitoring device wherein the means for inputting alcoholic beverage information includes means for inputting the volume of the alcoholic beverage per drink and the alcoholic content of the alcoholic beverage. In addition, the means for inputting body characteristic information includes means for inputting the weight of the individual and the gender of the individual.

It is also an object of the present invention to provide a blood alcohol content monitoring device wherein the means for calculating the blood alcohol content of the individual employs information regarding the volume of the alcoholic beverage per drink, the alcoholic content of the alcoholic beverage, the weight of the individual and the gender of the individual to determine the blood alcohol content of the individual.

It is another object of the present invention to provide a blood alcohol content monitoring device wherein the device includes a standard mode in which the individual is provided with blood alcohol content information and related warnings and a novelty mode in which the device prompts the individual with a variety of displays based upon the calculated blood alcohol content of the individual.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
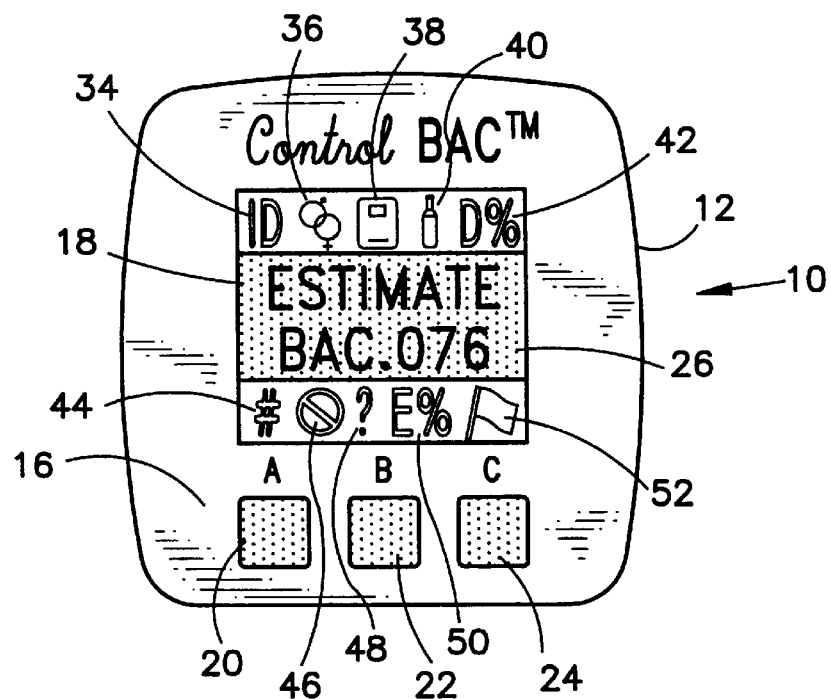
FIG. 1 is a front view of the blood alcohol content monitoring device in accordance with the present invention.
Figure 17:
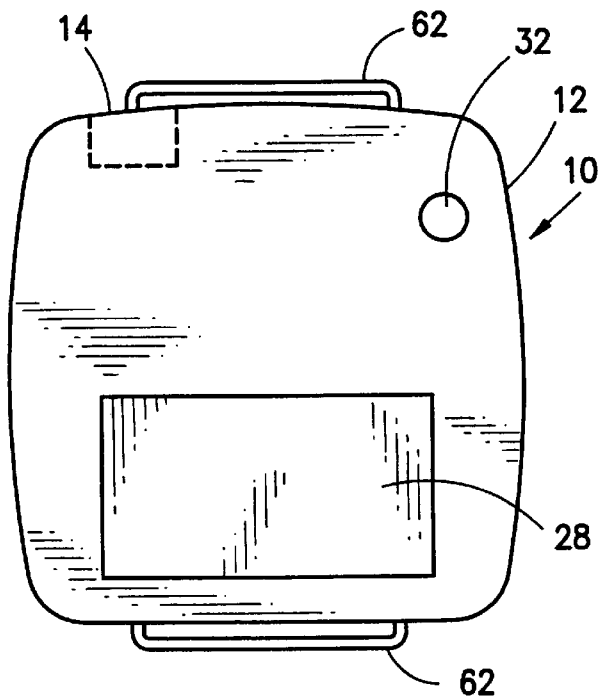
FIG. 17 is a back view of the blood alcohol content monitoring device in accordance with the present invention.
Figure 18:
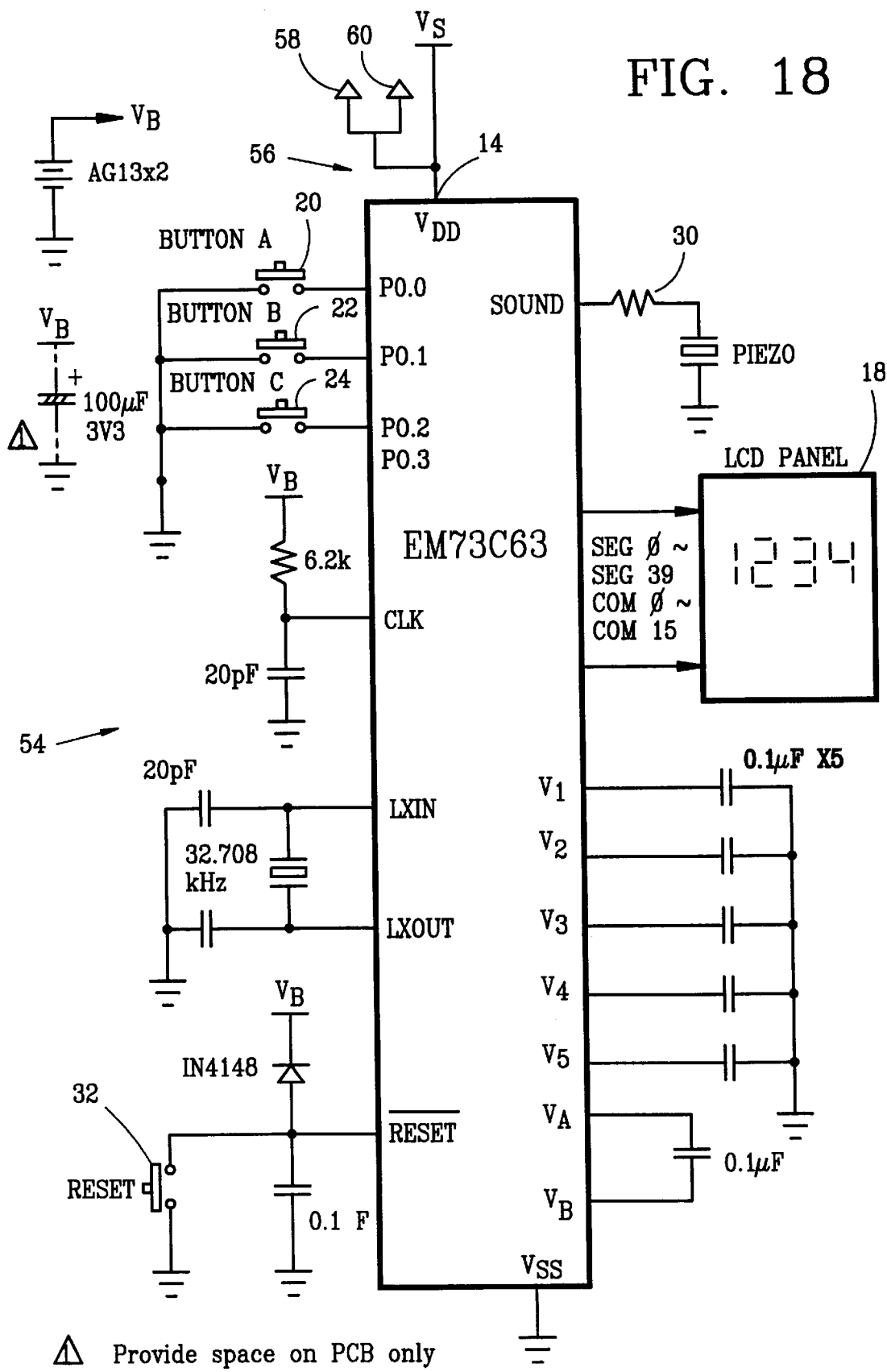
FIG. 18 is a schematic of the electronics employed in the present invention.

With reference to FIGS. 1, 17 and 18, a blood alcohol content monitoring device 10 in accordance with the present invention is disclosed. The device includes a two-piece case 12 formed with a socket 14 adapted to accommodate data input/output, visual indicators or other accessories that may be advantageously used with the present monitoring device 10. The use of the socket 14 for data input/output and with a visual indicator will be described in greater detail below. The monitoring device 10 further includes a user interface 16 including a liquid crystal display 18 and three control keys 20, 22, 24. The display 18 is a conventional LCD display employed in many pocket sized electronic devices, and a variety of displays may be employed without departing from the spirit of the present invention.

The display 18 includes a central area 26 in which information is displayed to the user and a plurality of information icons surrounding the central area. The three control keys include a scroll "+", also referred to as the "A" key 20, an enter key, also referred to as the "B" key 22, and a scroll "−" key, also referred to as the "C" key 24. The control keys are employed to select various items from menus presented during operation of the present blood alcohol content monitoring device 10.

The blood alcohol content monitoring device 10 is also provided with a battery cover 28, a buzzer 30 which provides users with various warnings during the operation of the device, and a system reset button 32.

With regard to the various icons displayed on the perimeter of the liquid crystal display 18, they identify the following subject matter:

ID USER ID (3 letters) (34)

⚥ USER'S GENDER (Male or Female) (36)

▯ USER'S WEIGHT (38)

🍸 USER'S SELECTED DRINK (40)

D% DESIRED BLOOD ALCOHOL CONTENT (42)

NUMBER OF DRINKS CONSUMED (44)

⊕ ELAPSED TIME FROM FIRST DRINK (46)

? DATA REGARDING CURRENT AND FUTURE STATUS (48)

E% ESTIMATED CURRENT BLOOD ALCOHOL CONTENT (50)

↻RESET OF BLOOD ALCOHOL CONTENT, TIME AND # OF DRINKS TO ZERO (Warm Start) (52)

Figure 19:
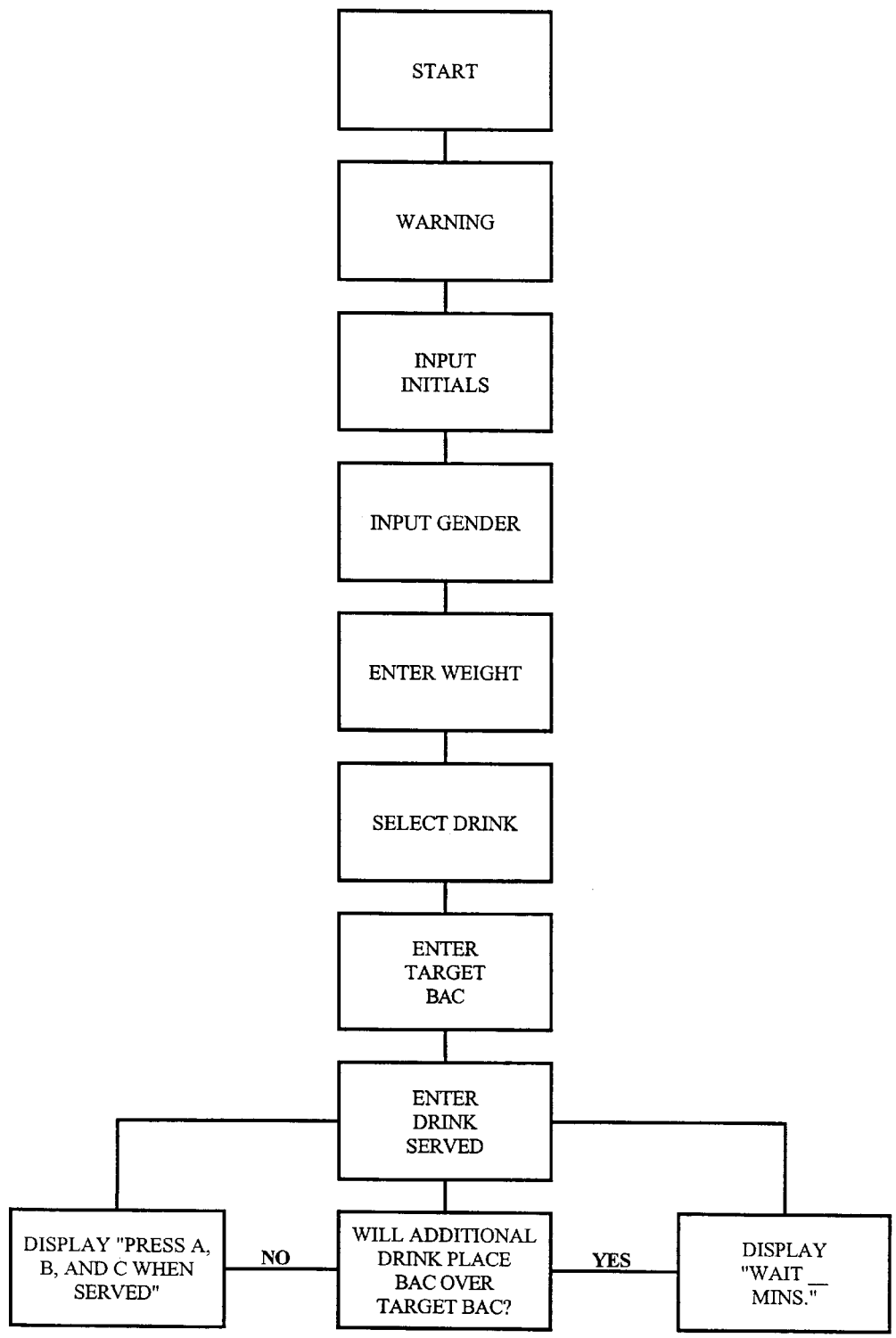
FIG. 19 is a flow chart of the operation of the present invention.

Operation of the system will now be described with reference to the flow chart set forth in FIG. 19. The system is initiated by either replacing the battery or pressing the system reset button 32. When the program starts, the display 18 signals the user with the following warning: "CAUTION WARNING BAC [Blood Alcohol Content] RESULTS ARE AN ESTIMATE TO BE USED AS A GUIDE ONLY. BAC LEVELS MAY VARY FROM PERSON TO PERSON. CERTAIN MEDICINES AND/OR POOR LIVER FUNCTIONS INCREASE BAC".

Figure 2:
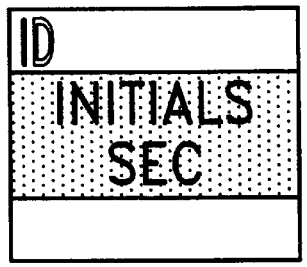
FIGS. 2–16 are display prompts used in accordance with the present invention.

Once the initial warning is presented, the USER ID icon 34 illuminates, and the device 10 requests that the user input his or her initials. The prompt employed to request the user's initials is a conventional initial input display utilized in many electronic devices requiring that a user input initials prior to use, and is shown in FIG. 2. While the prompt disclosed in FIG. 2 is the preferred prompt for requesting the desired ID information, a wide variety of prompts may be employed without departing from the spirit of the present invention. The possibility of varying the disclosed prompt applies for the many prompts discussed below. As such, many of the prompts discussed below may be varied without departing from the spirit of the present invention.

As those of ordinary skill in the art will appreciate, the user's first initial is input by scrolling through the letters of the alphabet using the "A" key 20 and/or the "C" key 24. Once the user employs the "A" key 20 and the "C" key 24 to display the user's first initial, the user simply presses the enter key 22 and the display moves to the second initial of the user. The second initial is input in a similar manner, and the third initial is similarly input.

Figure 3:
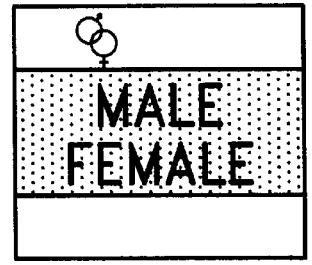

Once the initials of the user are input, the GENDER icon 36 is illuminated and the user receives a prompt requesting that his or her gender be input. A prompt as shown in FIG. 3 is preferably employed to request the user's gender. The user's gender is input by employing the "A" and "C" keys 20, 24 to scroll up and down between male and female. Once an appropriate gender is selected, the "B" enter key 22 is pressed to enter the user's gender.

Figure 4:
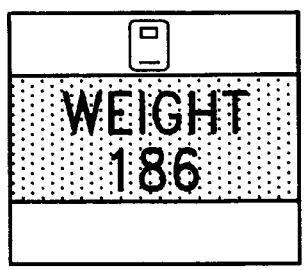
Figure 5:
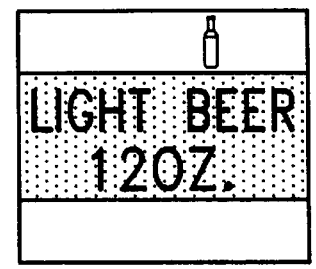
Figure 6:
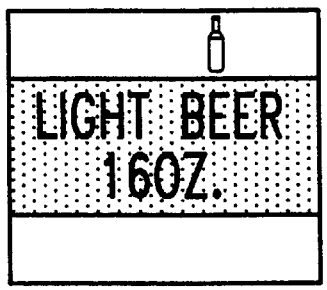
Figure 7:
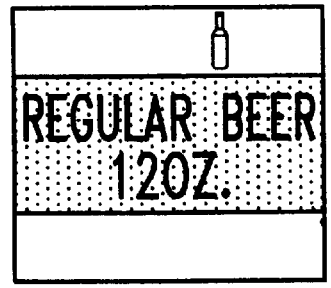
Figure 8:
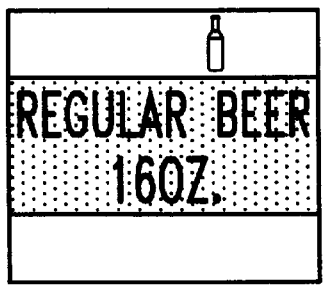
Figure 9:
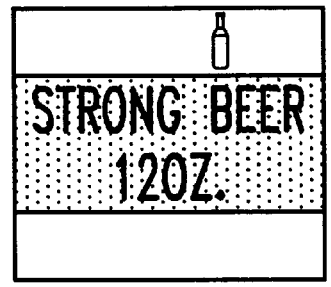
Figure 10:
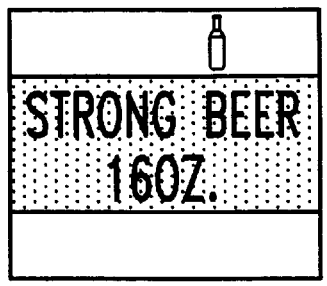

The user is then prompted to enter his or her weight. The user is prompted to enter weight information by the display shown in FIG. 4 and illumination of the USER'S WEIGHT icon 38. As with the initials of the user, the user's weight is input by employing the "A" and "C" keys 20, 24 in combination with the "B" enter key 22.

After the user's weight is entered, the device 10 requests that the user enter his or her drink of choice. The user is prompted by illuminating the USER'S SELECTED DRINK icon 40, in combination with a prompt that moves through various drinks as the user manipulates the "A", "B" and "C" 20, 22, 24 keys. When the appropriate drink is identified using the "A" and "C" keys 20, 24, the user presses the "B" enter key 22. In accordance with the preferred embodiment of the present invention, the various prompts for selecting a drink of choice are shown in FIGS. 5 through 10.

Figure 11:
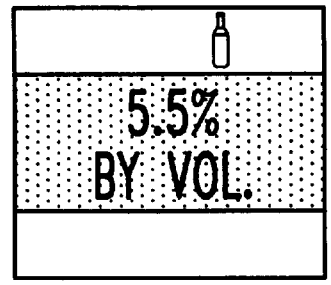

Once a drink is selected, the display 18 presents a prompt asking the user to confirm the appropriate alcohol content of the drink. For example, the prompt may be as shown in FIG. 11. In accordance with a preferred embodiment of the invention, the display indicates a default alcohol content of 5.5% when a strong drink is selected, a default alcohol content of 4.5% when a regular drink is selected and a default alcohol content of 4.0% when a light drink is selected. If the displayed alcohol content is correct, the user may simply push the "B" enter key 22. If, however, the displayed alcohol content is incorrect, the user alters the alcohol content by manipulating the "A" and "C" keys 20, 24 in combination with the "B" enter key 22.

Figure 12:
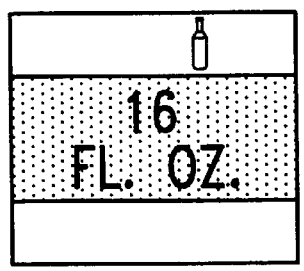

Once the alcohol content is confirmed, the display 18 prompts the user to confirm the size of the drink with a prompt as shown in FIG. 12. As such, and in accordance with the preferred embodiment of the present invention, the prompt indicates a default drink size of 16 ounces when a 16 ounce drink was previously selected and a default drink size of 12 ounces when a 12 ounce drink was previously selected. If the displayed drink size is correct, the user may simply push the "B" enter key 22. If, however, the displayed drink size is incorrect, the user alters the drink size by manipulating the "A" and "C" keys 20, 24 in combination with the "B" enter key 22.

Figure 13:
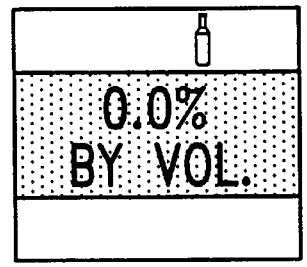
Figure 14:
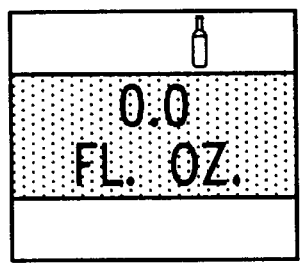

If none of the drink choices discussed above fit the requirements of the user, the user may scroll through the six prompts discussed above and enter the alcohol content and drink size without the use of the various prompts. Specifically, the user will receive a prompt as shown in FIG. 13 when he or she has scrolled past the six choices discussed above. The prompt asks the user to enter the alcohol content of the drink by manipulating the "A" and "C" keys 20, 24. Once the appropriate alcohol content is entered by pressing the "B" enter key 22, the user receives a second prompt as shown in FIG. 14 asking that the drink size be entered. The drink size is then entered by manipulating the "A", "B" and "C" keys 20, 22, 24.

Figure 15:
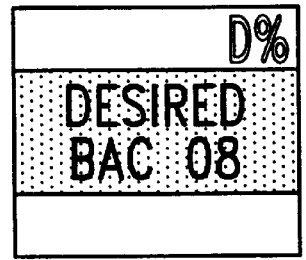

Once the selected drink is input, the device prompts the user to input the desired target blood alcohol content with the prompt shown in FIG. 15. The default display shows a blood alcohol content of 0.080%. If this is acceptable, the user simply presses the "B" enter key 22. If, however, the target blood alcohol content needs to be adjusted, the user employs the "A" and/or "C" keys 20, 24 to manipulate the target blood alcohol content. In accordance with the preferred embodiment of the present invention, the target blood alcohol content may be varied between 0.000% and 0.150%, although other ranges may be employed without departing from the spirit of the present invention.

As will be discussed in greater detail below, the target blood alcohol content is used to provide user's with a warning when the target blood alcohol content will be reached by the user when an additional drink is consumed. With this in mind, it is the intent of the present invention that the target blood alcohol content be set to the user's state limit for legal intoxication. However, users may input a variety of target blood alcohol contents depending upon their specific needs.

After the target blood alcohol content is input, the present device is ready to begin monitoring the user's blood alcohol content. At this time, the DATA REGARDING CURRENT AND FUTURE STATUS icon 48 is illuminated and the display 18 presents the following information: "ESTIMATE YOUR BAC IS 0.000 NOW. PRESS A, B AND C WHEN SERVED. ESTIMATE NEXT DRINK WOULD MAKE BAC 0.020" (or whatever the estimated blood alcohol content of the user is based upon the drink selected and the user information). This prompts the user to press the "A", "B" and "C" keys 20, 22, 24 when the first drink is served.

In accordance with the preferred embodiment of the present invention, the message is split between multiple screens which scroll one after the other to provide the user with the desired message. While multiple screens are used in accordance with the preferred embodiment of the present invention, other display protocols could be employed without departing from the spirit of the present invention. The message may be repeated at any time by using the "A" and "C" 20, 24 keys to select and illuminate the DATA REGARDING CURRENT AND FUTURE STATUS icon 48.

If the "A", "B" and "C" keys 20, 22, 24 are pushed together, the buzzer 30 and display 18 confirm the entry of a drink. Specifically, the buzzer 30 alerts the user with a plurality of beeps and the display 18 prompts the user with a message stating "DRINK ENTERED". The DATA REGARDING CURRENT AND FUTURE STATUS icon 48 is then illuminated and the display 18 presents the following message: "ESTIMATE YOUR BAC IS 0.020 NOW. PRESS A, B AND C WHEN SERVED. ESTIMATE NEXT DRINK WOULD MAKE BAC 0.040. YOU ARE IMPAIRED BE VERY CAREFUL" (or whatever the estimated blood alcohol content of the user is based upon the drink selected and the user information). The warning "YOU ARE IMPAIRED BE VERY CAREFUL" is added to the prompt associated with the DATA REGARDING CURRENT AND FUTURE STATUS icon 48 any time the user registers a blood alcohol content above zero. As discussed below in greater detail, the present device 10 employs the input information to monitor the blood alcohol content of the user based upon known scientific information.

After the device delivers the message associated with the DATA REGARDING CURRENT AND FUTURE STATUS icon 48, the ESTIMATED CURRENT BLOOD ALCOHOL CONTENT icon 50 is illuminated and the display 18 presents the message "ESTIMATE BAC 0.020". As drinks are entered, the message associated with the DATA REGARDING CURRENT AND FUTURE STATUS icon 48 varies depending upon whether the user's blood alcohol content exceeds the target blood alcohol content previously entered. Specifically, the message "PRESS A, B AND C WHEN SERVED" is replaced with "WAIT --- MIN." when the users blood alcohol content will exceed the target blood alcohol content if the user has an additional drink.

That is, the message "PRESS A, B AND C WHEN SERVED" is displayed if the user's current blood alcohol content plus one drink is less than the target blood alcohol content. This tells the user that he or she may have an additional drink without exceeding the target blood alcohol content.

In contrast, the "WAIT --- MIN." message is displayed when the user's current blood alcohol content plus one drink is greater than the previously entered target blood alcohol content. In this way, the present device provides a user with a warning that an additional drink will place the user over the target blood alcohol content and the user should wait a specified time to avoid exceeding the target blood alcohol content. For example, if the user must wait 40 minutes or an additional drink will place his or her blood alcohol content over the target blood alcohol content, the displayed message will be "WAIT 040 MIN.".

If a user wishes to receive an estimate of his or her current blood alcohol content, he or she may simply utilize the "A" and/or "C" keys 20, 24 to illuminate the icons until the ESTIMATED CURRENT BLOOD ALCOHOL CONTENT icon 50 is illuminated. At this time, the display will provide the user with a display stating "ESTIMATE BAC .[user's blood alcohol content]". The user may also display his or her blood alcohol content by illuminating the DATA REGARDING CURRENT AND FUTURE STATUS icon 48 at which time the user will receive the following message: "ESTIMATE YOUR BAC IS .[user's blood alcohol content] NOW. PRESS A, B AND C WHEN SERVED. ESTIMATE NEXT DRINK WOULD MAKE BAC .[user's estimated blood alcohol content]. YOU ARE IMPAIRED BE VERY CAREFUL" or "ESTIMATE YOUR BAC IS .[user's blood alcohol content] NOW. WAIT [time user must wait] MIN. ESTIMATE NEXT DRINK WOULD MAKE BAC .[user's estimated blood alcohol content]. YOU ARE IMPAIRED BE VERY CAREFUL".

During operation of the device, the various input information my be altered by moving from icon to icon using the "A" and "C" keys 20, 24. Once an icon is illuminated, the relevant data may be modified by pressing the "B" enter key 22 and then inputting the modified information in the manner discussed above. If vital data is changed by the user after the initial setting, any combination of the following messages may be displayed: "GENDER DATA WAS CHANGED" and/or "WEIGHT DATA WAS CHANGED"

and/or "BAC LIMIT DATA WAS CHANGED". The user may also change drink information in the same manner the user may change personal information. If the user chooses to change drinks, he or she need only reenter the new drink and the device 10 will continue to monitor blood alcohol content based upon the new drink information entered by the user.

In addition, the device may display a final warning as follows: "CAUTION WARNING BAC RESULTS ARE AN ESTIMATE TO BE USED AS A GUIDE ONLY". If during operation, no keys are pushed, the LCD goes off after 30 seconds of inactivity. Once the "A", "B" and "C" are pushed together, the DATA REGARDING CURRENT AND FUTURE STATUS icon 48 illuminates and the system returns to present the message associated with icon 48.

Figure 16:
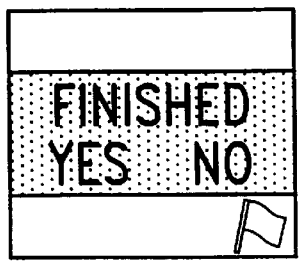

As discussed above, the various icons may be selected using the "A" and/or "C" keys 20, 24. If the NUMBER OF DRINKS CONSUMED icon 44 is selected the display will show the user the number of drinks consumed. Similarly, if the ELAPSED TIME FROM FIRST DRINK icon 46 is selected, the device will display the elapsed time the user has been drinking. As discussed above, the RESET icon 52 is a reset for the blood alcohol content, time, and number of drinks. When the RESET icon 52 is selected, a display prompts the user as to whether he or she is finished. A preferred display for prompting a user when he or she is finished is shown in FIG. 16. The user employs the "A" and "C" keys 20, 24 to then select whether he or she is finished drinking. If "YES" is selected by pushing the "B" enter key, then the number of drinks, time, and blood alcohol content are reset to zero and the LCD goes off. If "NO" is selected, the device continues monitoring blood alcohol content based upon the previously entered information.

In addition to providing users with serious information regarding their blood alcohol content, the present device also includes a message mode. The message mode is entered by selecting a weight of 999 during the initial set up. When a weight of 999 is selected, the device enters the message mode. Once 999 is entered, the device prompts the user to enter his or her correct weight, and the user proceeds to enter required user information. After the required information is input, the following messages are presented depending upon the blood alcohol content of the user:

| BAC | MESSAGE |
| --- | --- |
| .001–.030 | HERE WE GO |
| .031–.040 | TASTES SO GOOD |
| .041–.050 | NO PROBLEM |
| .051–.060 | FEELING GOOD |
| .061–.075 | NEARING THE BUZZ ZONE |
| .076–.090 | DON'T WORRY BE HAPPY |
| .091–.100 | YOU'RE IN THE BUZZ ZONE |
| .101–.110 | THAT'S ENOUGH |
| .111–.120 | SLOW DOWN |
| .121–.130 | I SAID THAT'S ENOUGH |
| .131–.140 | YOU'RE WAY TOO LOADED |
| .141–.150 | DRUNK ONCE AGAIN |
| .151–.160 | DOUBLE VISION DOUBLE VISION |
| .161–.170 | TRY CLOSING ONE EYE |
| .171–.180 | IT WON'T BE LONG NOW |
| .181–.190 | ONE MORE DRINK FOOL WILL DROWN YOU |
| .191–.220 | YOU ARE HANK THE DWARF |
| .221 & UP | YOU SHOULD JOIN AA |

With reference to FIG. 18, the circuitry employed in the present device 10 is disclosed. As discussed above, the device includes "A", "B" and "C" keys 20, 22, 24, as well as a reset button 32. The device further employs a microcontroller 54. In accordance with the preferred embodiment of the present invention, an EM73C634 bit microcontroller from Elan Microelectronics Inc. is employed.

The microcontroller 54 includes a clock function allowing the device to monitor the passage of time in a manner required for the proper operation of the present blood alcohol content monitoring device 10. The microcontroller 54 is connected to the LCD panel 18 in a manner permitting desired displays to be input thereon. The LCD panel 18 is preferably a 16 ×35 panel commonly found in small electronic displays.

In use, the software is masked onto the microprocessor 54 such that the device 10 operates in the manner discussed above. The code permits the present device 10 to monitor the blood alcohol content of users over time based upon the input information discussed above and well known scientific information regarding the processing of alcohol by the human body. The formula employed by the present invention is disclosed in the attached code and other formulas may be employed without departing from the spirit of the present invention. While a specific software is disclosed for achieving the present invention, the software may be varied without departing from the spirit of the present invention.

If an individual wishes to modify data within the RAM of the microcontroller 54 or download data from the RAM or ROM of the microcontroller 54, the data may be input or output using the socket 14 previously discussed. For example, the software may be varied to change the messages displayed by the present blood alcohol content monitoring device 10 or to change the equations used in monitoring the blood alcohol content of those using the present blood alcohol content monitoring device 10. In addition, a visual indicator 56 may be coupled to the socket 14, permitting the device 10 to provide the user with a visual indication of the user's blood alcohol content status. For example, the visual indicator 56 may have a red LED 58 used to warn the user that he or she should wait before consuming another drink and a green LED 60 used to inform a user that he or she may continue drinking.

The present blood alcohol content monitoring device 10 is intended to be used as a keychain. However, the housing includes slots 62 on opposite edges thereof through which a watch band may be installed. Since the device 10 includes a clock function it may be used as a watch by simply varying the software to display the time.

While the preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A blood alcohol content monitoring device, comprising:

means for storing body characteristic information of an individual;

means for storing information regarding an alcoholic beverage;

a clock means for measuring the passage of time;

an interface permitting the individual to input body characteristic information and alcoholic beverage information;

calculation means for calculating the blood alcohol content of the individual based upon body characteristic information, alcoholic beverage information and the passage of time, wherein the calculation means also estimates the blood alcohol content of an individual if the individual were to have an additional drink without inputting the additional drink; and display means for providing the individual with information regarding blood alcohol content based upon the body characteristic information, alcoholic beverage information and the passage of time, the display means also providing the individual with a message regarding the estimated blood alcohol content if the individual were to have an additional drink.

2. The blood alcohol content monitoring device according to claim 1, wherein the display means provides the blood alcohol content of the individual if the individual were to have an additional drink.

3. The blood alcohol content monitoring device according to claim 1, wherein the calculation means also determines when an individual will exceed a target blood alcohol content by having an additional drink and the display means provides the individual with a warning when the individual will exceed the target blood alcohol content by having an additional drink.

4. The blood alcohol content monitoring device according to claim 3, wherein the interface means includes means for inputting the target blood alcohol content at which point the display means will provide the individual with a warning when the individual will exceed the target blood alcohol content by having an additional drink, and the device further includes means for storing the target blood alcohol content.

5. The blood alcohol content monitoring device according to claim 4, wherein the warning includes a report as to how long the individual must wait before having an additional drink without exceeding the target blood alcohol content.

6. The blood alcohol content monitoring device according to claim 1, wherein the interface means includes a plurality of icons used to prompt an individual to input body characteristic information and alcoholic beverage information.

7. The blood alcohol content monitoring device according to claim 1, wherein the interface means includes at most three keys for inputting body characteristic information and alcoholic beverage information.

8. The blood alcohol content monitoring device according to claim 1, wherein the means for inputting alcoholic beverage information includes means for inputting the volume of the alcoholic beverage per drink and the alcoholic content of the alcoholic beverage; and the means for inputting body characteristic information includes means for inputting the weight of the individual and the gender of the individual.

9. The blood alcohol content monitoring device according to claim 8, wherein the means for calculating the blood alcohol content of the individual employs information regarding the volume of the alcoholic beverage per drink, the alcoholic content of the alcoholic beverage, the weight of the individual and the gender of the individual to determine the blood alcohol content of the individual.

10. The blood alcohol content monitoring device according to claim 1, further including a message mode in which the device prompts the individual with a variety of displays based upon the calculated blood alcohol content of the individual.

11. A blood alcohol content monitoring device, comprising:
 a microcontroller for storing body characteristic information of an individual and alcoholic beverage information;
 a clock means for measuring the passage of time;
 a user interface coupled to the microcontroller such that a user may input body characteristic information and alcoholic beverage information for use by the microcontroller;
 the microcontroller further including calculation means for calculating the blood alcohol content of the individual based upon body characteristic information, alcoholic beverage information and the passage of time, wherein the calculation means also estimates the blood alcohol content of an individual if the individual were to have an additional drink without inputting the additinal drink; and
 wherein the user interface includes a display coupled to the microcontroller for providing the individual with information regarding blood alcohol content based upon the body characteristic information, alcoholic beverage information and the passage of time, the display also providing the individual with a message regarding the estimated blood alcohol content if the individual were to have an additional drink.

12. The blood alcohol content monitoring device according to claim 11, wherein the display provides the blood alcohol content of the individual if the individual were to have an additional drink.

13. The blood alcohol content monitoring device according to claim 11, wherein the calculation means also determines when an individual will exceed a target blood alcohol content by having an additional drink and the display provides the individual with a warning when the individual will exceed the target blood alcohol content by having an additional drink.

14. The blood alcohol content monitoring device according to claim 13, wherein the microcontroller further stores the target blood alcohol content and the user interface includes means for inputting the target blood alcohol content, wherein the display provides the individual with a warning when the individual will exceed the target blood alcohol content by having an additional drink.

15. The blood alcohol content monitoring device according to claim 14, wherein the warning includes a report as to how long the individual must wait before having an additional drink without exceeding the target blood alcohol content.

16. The blood alcohol content monitoring device according to claim 11, wherein the user interface includes a plurality of icons used to prompt an individual to input body characteristic information and alcoholic beverage information.

17. The blood alcohol content monitoring device according to claim 11, wherein the user interface includes at most three keys for inputting body characteristic information and alcoholic beverage information.

18. The blood alcohol content monitoring device according to claim 11, wherein the means for inputting alcoholic beverage information includes means for inputting the volume of the alcoholic beverage per drink and the alcoholic content of the alcoholic beverage; and the means for inputting body characteristic information includes means for inputting the weight of the individual and the gender of the individual.

19. The blood alcohol content monitoring device according to claim 18, wherein the means for calculating the blood alcohol content of the individual employs information regarding the volume of the alcoholic beverage per drink, the alcoholic content of the alcoholic beverage, the weight of the individual and the gender of the individual to determine the blood alcohol content of the individual.

20. The blood alcohol content monitoring device according to claim 11, wherein the device includes a standard mode in which the individual is provided with blood alcohol content information and related warning and a novelty mode in which the device prompts the individual with a variety of displays based upon the calculated blood alcohol content of the individual.

* * * * *